United States Patent [19]

Devanathan et al.

[11] Patent Number: 5,672,284

[45] Date of Patent: Sep. 30, 1997

[54] METHOD OF MAKING ORTHOPAEDIC IMPLANT BY WELDING

[75] Inventors: Deva Devanathan, Warsaw; Steve Krebs; Steve T. Lin, both of Fort Wayne; James J. Morr, Leesburg; Clarence M. Panchison, Warsaw, all of Ind.

[73] Assignee: Zimmer, Inc., Warsaw, Ind.

[21] Appl. No.: 609,210

[22] Filed: Mar. 1, 1996

Related U.S. Application Data

[62] Division of Ser. No. 228,774, Apr. 18, 1994, Pat. No. 5,504,300.

[51] Int. Cl.$^6$ .................................................. B23K 26/00
[52] U.S. Cl. ............................ 219/121.64; 219/137 R; 228/173.1; 228/182; 623/22; 623/901
[58] Field of Search .......................... 219/117.1, 137.12, 219/121.14, 121.64, 121.63, 121.13, 121.85; 623/22, 23, 901; 228/173.1, 182

[56] References Cited

U.S. PATENT DOCUMENTS

| 3,605,123 | 9/1971 | Hahn . | |
|---|---|---|---|
| 3,855,638 | 12/1974 | Pilliar . | |
| 3,905,777 | 9/1975 | Lacroix | 428/550 |
| 4,261,063 | 4/1981 | Blanquaert | 623/23 |
| 4,536,894 | 8/1985 | Galante et al. | 623/22 |
| 4,636,219 | 1/1987 | Pratt et al. | 623/22 |
| 4,660,755 | 4/1987 | Farling et al. | 228/178 |
| 4,693,721 | 9/1987 | Ducheyne | 623/16 |
| 4,718,914 | 1/1988 | Frey et al. | 623/23 |
| 4,728,335 | 3/1988 | Jurgutis | 623/23 |
| 4,813,963 | 3/1989 | Hori et al. | 623/23 |
| 4,828,566 | 5/1989 | Griss | 623/23 |
| 4,835,357 | 5/1989 | Schalk | 219/121.64 |
| 4,863,484 | 9/1989 | Brown et al. | 623/16 |
| 4,969,904 | 11/1990 | Koch et al. | 623/16 |
| 4,976,738 | 12/1990 | Frey et al. | 623/23 |
| 5,013,324 | 5/1991 | Zolman et al. | 623/23 |
| 5,015,817 | 5/1991 | Kranz | 219/121.14 |
| 5,027,998 | 7/1991 | Bugle | 228/44.5 |
| 5,030,233 | 7/1991 | Ducheyne | 623/16 |
| 5,057,108 | 10/1991 | Shetty et al. | 606/53 |
| 5,080,674 | 1/1992 | Jacobs et al. | 623/20 |
| 5,108,432 | 4/1992 | Gustavson | 623/16 |
| 5,139,528 | 8/1992 | Koch et al. | 623/66 |
| 5,171,148 | 12/1992 | Wasserman et al. | 433/215 |
| 5,198,308 | 3/1993 | Shetty et al. | 428/608 |
| 5,242,706 | 9/1993 | Cotell et al. . | |
| 5,245,155 | 9/1993 | Pratt et al. | 219/121.63 |
| 5,397,359 | 3/1995 | Mittelmeier et al. | 623/16 |
| 5,443,510 | 8/1995 | Shetty et al. | 623/23 |
| 5,496,375 | 3/1996 | Sisk et al. | 623/23 |

FOREIGN PATENT DOCUMENTS

| 0 191 182 | 8/1986 | European Pat. Off. . |
| 0 273 871 | 7/1988 | European Pat. Off. . |
| 0 560 418 | 9/1993 | European Pat. Off. . |
| 0 599 426 | 6/1994 | European Pat. Off. . |
| 0 623 687 | 11/1994 | European Pat. Off. . |
| 64-2645 | 4/1989 | Japan . |

OTHER PUBLICATIONS

B. Bryan et al., "Welding Processes; current status, developments and future trends," *New Metallic Materils and New Fabrication Processes*, 1987, pp. 3.1–3.36.

(List continued on next page.)

*Primary Examiner*—Teresa J. Walberg
*Assistant Examiner*—Gregory L. Mills
*Attorney, Agent, or Firm*—Todd A. Dawson

[57] ABSTRACT

A method of forming an orthopaedic implant having a porous surface, the method including the steps of providing a porous surface including a porous layer attached to a substantially solid layer; positioning the porous layer on the orthopaedic implant; providing a high energy density welding device capable of producing a high energy density weld beam; and forming a weld bead substantially about the periphery of the porous layer by directing the high energy density weld beam about the periphery of the porous layer, wherein the weld bead bonds the porous layer to the implant. Two shaped porous pads may also be welded together about an implant body to avoid welding the body itself.

3 Claims, 6 Drawing Sheets

OTHER PUBLICATIONS

U. Dilthey and A. Risch, "Laser Welding of Stainless Steels and Stainless/low–alloy Material Combinations," *Welding in the World*, 1995, pp. 135–142.

Metzbower et al., "Depth of Penetration in Laser Beam Welding," *Laser Materials Processing*, 1994, pp. 203–212.

P. Khan and A. Paul, "Experimental and Theoretical Evaluation of Mass Transport During Laser Welding," *International Conference on Beam Processing of Advanced Materials*, 1992, pp. 217–227.

Bagdasarov et al., "1 kW Processing YAG Laser," *Paton Welding Journal* 1991, pp. 310–312.

Balbi et al., "Laser Repairing Techniques for Superalloy Components," *Metallurgical Science and Technology*, 1992, pp. 56–64.

Matsuda et al., "Solidification Crace Susceptibility of Laser Weld Metal in 0.2C–Ni–Cr–Mo steels: Effects of Bead Configuration and S and P Contents," *Welding International*, 1993, pp. 686–692.

Z. Sun and T. Moisio, "A Comparitive Study of Dissimilar Metal Welding Using Various Processes," *International Trends in Welding Science and Technology*, 1993, pp. 433–438.

Von W. Dick and E. Morscher, "Experiences With the Development of Non–cemented Prostheses, "*Medizinische–Orthopadische Technik*, 1986, pp. 6–10.

Ignatiev, et al., "The High Speed Pyrometer System for Laser Welding, Cutting, Heat Treatment and Alloying Processes Temperature Control," *Laser Treatment of Materials Processing ECLAT*, 1992, pp. 15–20.

Sun et al., "Weld Metal/ferritic Steel Interface in Laser Welded Austenitic/ferritic Dissimilar Steel Joints," *Journal of Materials Science Letters* 13, 1994, pp. 802–805.

Zheng Sun, "Residual Stress in Laser Welded Dissimilar Steel Tube–to–Tube Joints," *Scripta Mettalurgica et Materialia*, 1993, pp. 633–637.

J.M. Pettetier and M. Robin, "Metal–ceramic Joining by Laser," *Journal De Physique IV*, 1993, pp. 1061–1064.

A. Paul and P. Khan, "Mass Transport During Laser Welding of Stainless Steels and alloys Used by U.S. Navy," *Journal of Laser Applications*, 1994, pp. 32–37.

Bob Irving, "Laser Beam and GMA Welding Lines Go On–Stream at Arvin Industries," *Welding Journal*, 1993, pp. 47–50.

C.J. Dawes, "Materials," *Laser Welding—A Pracical Guide*, 1992, pp. 51–77.

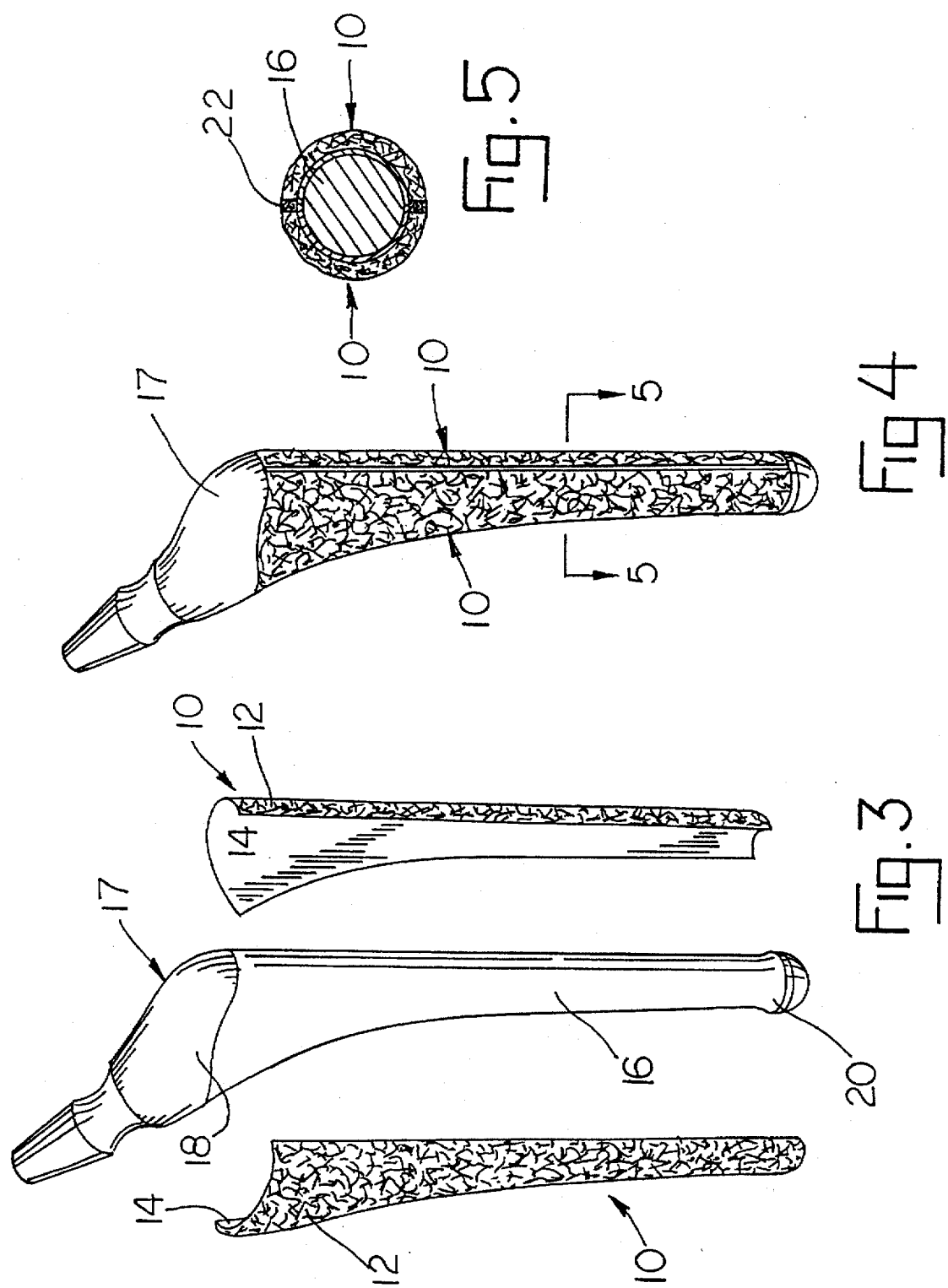

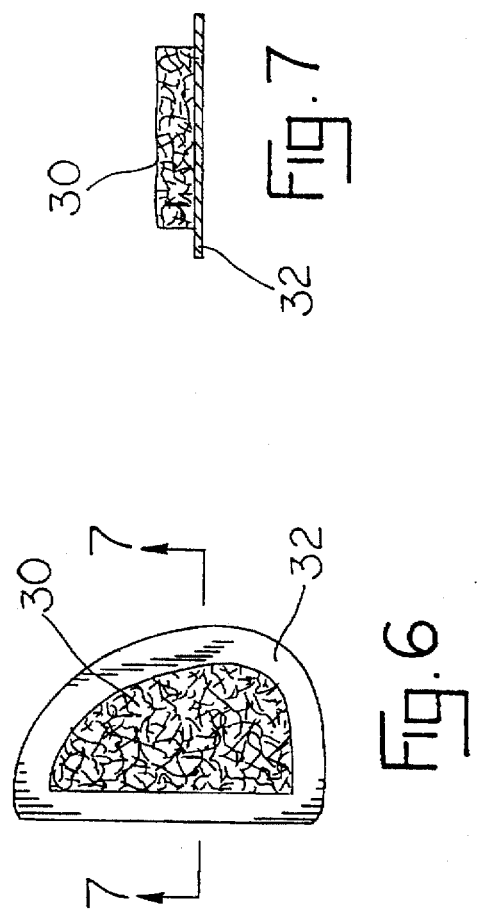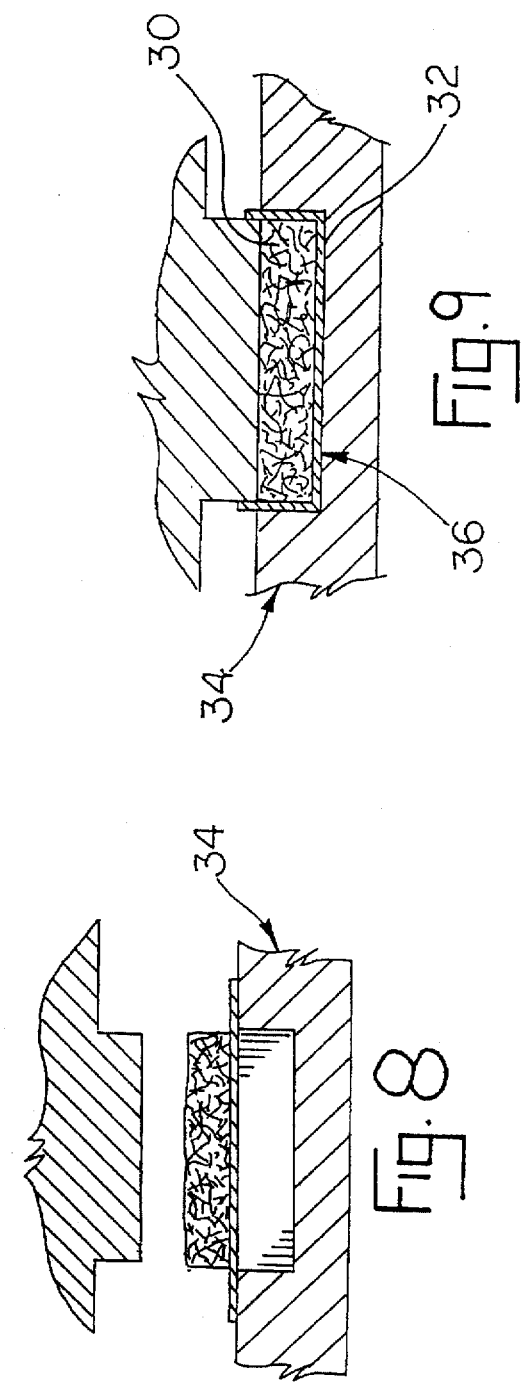

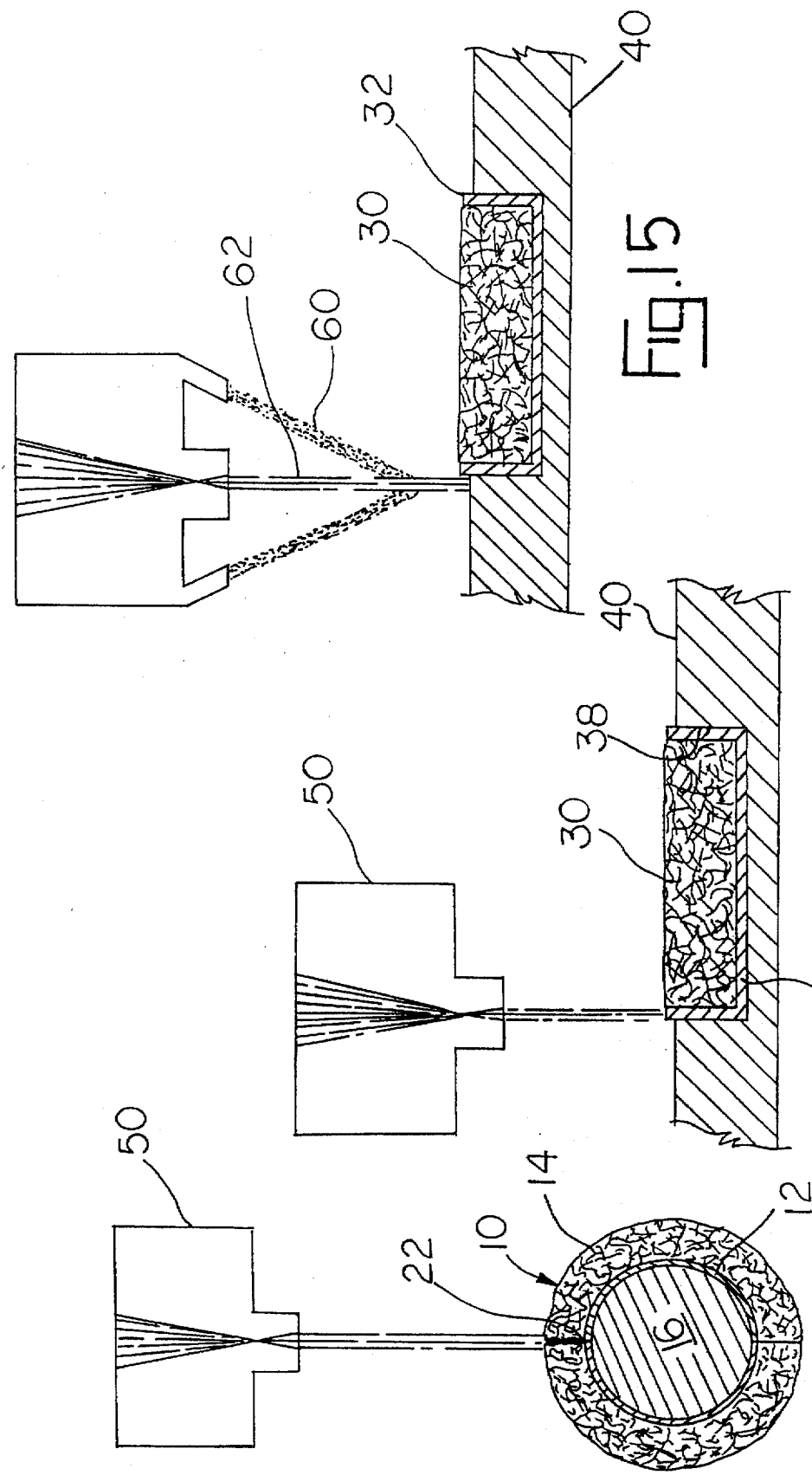

METHOD OF MAKING ORTHOPAEDIC IMPLANT BY WELDING

This is a division of application Ser. No. 08/228,774 filed Apr. 18, 1994 now U.S. Pat. No. 5,504,300.

FIELD OF THE INVENTION

This invention relates to orthopaedic implants having a porous outer layer and has specific relevance to an implant having a porous layer attached to the implant body by welding.

BACKGROUND OF THE INVENTION

It is known to have a portion of an orthopaedic implant covered by a porous layer to promote the ingrowth of bone within the openings of the porous layer for long term fixation of the implant to the bone. Diffusion bonding is the most widely known and accepted method of attaching the porous layer to the implant. Diffusion bonding a porous layer to a substrate on a curved surface, such as a portion of a hip stem, is a time-consuming and expensive task. Further, diffusion bonding a porous material to a substrate can cause notches to be formed in the substrate, thereby decreasing the strength of the substrate. To compensate for this effect, orthopaedic implant manufactures may either limit the amount of the porous layer attached to the substrate or adjust the size of the substrate to increase its strength.

SUMMARY OF THE INVENTION

The method and implant of this invention provide for the attachment of a porous pad to the implant by laser welding. The porous pad is comprised of a flat sheet of porous material that is diffusion bonded to a thin metal foil layer. Diffusion bonding between the flat foil to the porous material is substantially less troublesome than when bonding on a curved surface. After the metal foil is bonded to the porous material to form a porous pad, the pad is cut to the desired shape to form a blank. The blank is stamped into a shape substantially conforming to its intended location on the implant. The blank is positioned on the implant and laser welded to the substrate. If the porous surface is intended to surround a portion of the implant such as would be seem on a porous hip stem, a second blank is cut and stamped. The two stamped blanks are positioned about the implant such that they abut at their edges. The blanks are then welded together using a laser welder to form an integral porous layer about the implant. The porous pads may also be welded using the laser welder to the implant at their ends to seal the interface of the porous pad and implant. By first bonding the porous material to thin foil to form the pad and then connecting the blanks cut and stamped from the blanks to the implant by laser welding the formation of notches in the implant body is eliminated. The laser beam is controlled such that the substrate is not affected by the welding process. Therefore, by connecting the porous layer in this manner, the implant manufacturer is not limited as to the amount of porous surface that can be connected to the implant body. Further, laser welding a porous pad to the substrate is a quicker and less expensive method of attaching as compared to the diffusion bonding process.

In an alternative embodiment, a polymer layer could be positioned between the pad and substrate. The polymer layer would adhesively bond the pad and substrate together to eliminate the need for unique wilting clamps and also would assist in transferring stress to the substrate in a more uniform manner. The polymer would also assist in filling gaps between the pad and the substrate thereby allowing the manufacturer to reduce the manufacturing tolerances for the substrate and pad.

In a further variation of the invention, the thin metal foil may include small holes to allow the ingress and egress of fluid from the space between the pad and substrate.

The terms laser weld, laser welder or laser beam are used throughout this application to refer to any high energy density welding process such as laser or electron beam welding.

Accordingly, it is an advantage of this invention to provide for a novel orthopaedic implant having a porous surface layer connected to the implant body by welding.

Another advantage of the invention is to provide for a novel method of attaching a porous surface to an orthopaedic implant.

Yet another advantage of the invention is to provide a method of attaching a porous surface to an implant without detrimentally effecting the strength of the implant.

Another advantage of the invention is to provide an orthopaedic implant wherein the interface between the porous surface layer and the implant body is sealed.

Other advantages of this invention will become apparent upon a reading of the following description taken with the accompanying drawings.

BRIEF DESCRIPTION OF THE DRAWINGS

FIG. 3 is an exploded perspective view of a hip stem configured for accepting the shaped blanks of FIG. 2.

FIG. 4 is a perspective view of the hip stem and blanks of FIG. 3 after the welding process is complete.

FIG. 5 is a cross-sectional view taken along lines 5—5 of FIG. 4.

FIG. 6 is an elevational view of a substantially flat blank formed in an alternative manner such that the metal foil extends beyond the porous material.

FIG. 7 is a side elevational view of FIG. 6.

FIGS. 8 and 9 illustrate the shaping of the substantially flat blank of FIGS. 6 and 7 with a stamping die such that the foil extends along the side edges of the porous material.

FIG. 13 is a diagram illustrating the method of laser welding the porous pads to an implant. The implant and porous pads are illustrated in cross-section.

FIG. 14 is an enlarged cross sectional view of the area circled in FIG. 10 and identified by number 14.

FIG. 15 is a diagram illustrating a method for laser cladding the porous pads to the implant.

DESCRIPTION OF THE PREFERRED EMBODIMENTS

The preferred embodiments herein described are not intended to be exhaustive or to limit the invention to the precise forms disclosed. Rather, they are chosen and described to best explain the invention so that others skilled in the art might utilize their teachings.

Figure 1:
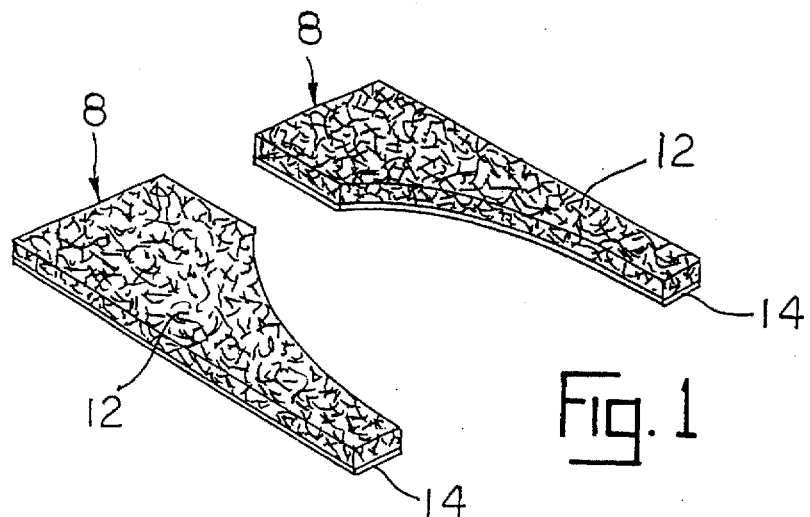
FIG. 1 is a perspective view of a substantially flat porous blank for a hip stem implant which has been cut from a larger porous pad.
Figure 2:
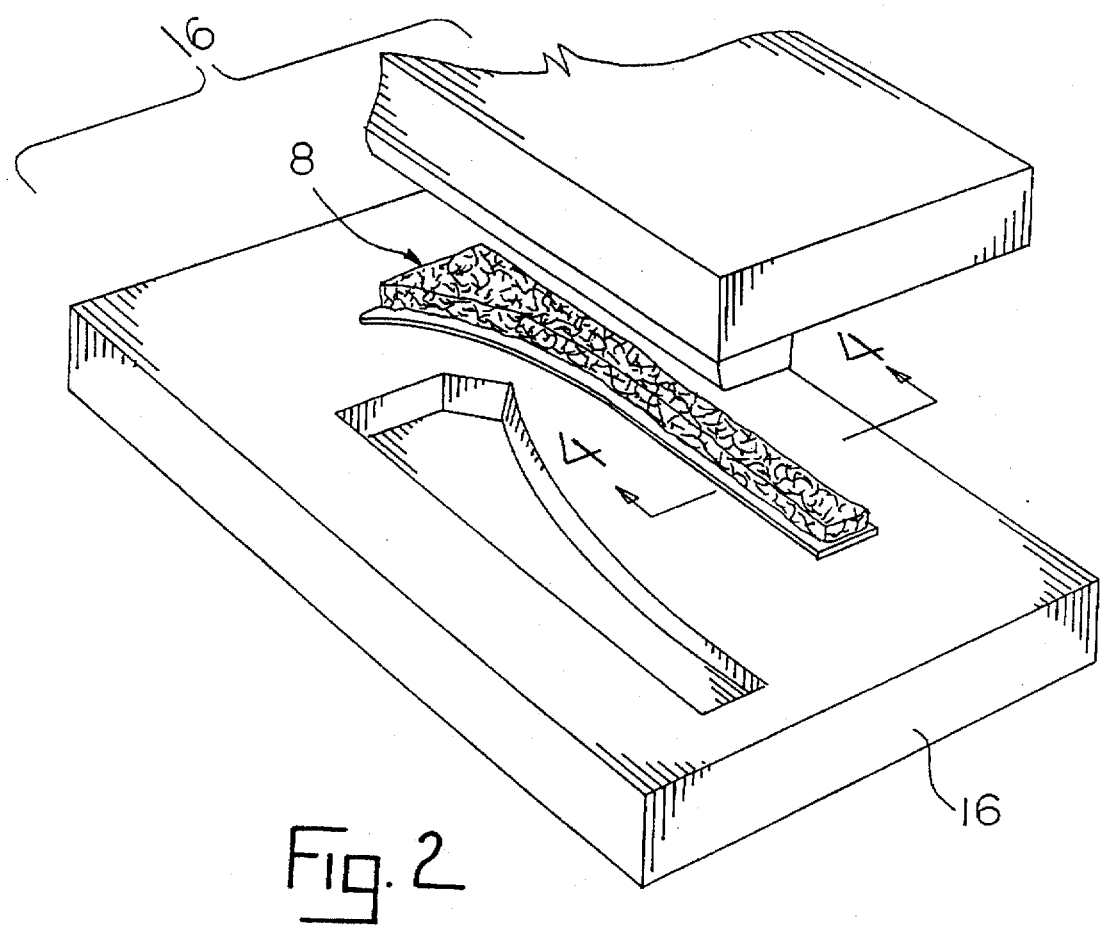
FIG. 2 is a perspective view illustrating the stamping process used to form the flat porous blank of FIG. 1 into the shape to fit a portion of a hip stem implant.

The methods of the invention are illustrated in the figures to yield an implant having a porous structure welded to the body of the implant. The method begins with the formation of a porous pad 10 having a porous surface 12 and a thin metal backing 14. Preferably, a large sheet of the porous material, such as fiber metal, is diffusion bonded to a similarly sized thin metal sheet or foil. After the diffusion bonding process, blanks 8 are cut from the sheet using laser cutting or a device which can cut through the pad without substantially deforming the edges of the blank. Blanks 8 are then placed within a stamping die 16 having cooperating male and female sections as illustrated in FIG. 2. Stamping die 16 includes cooperating male and female parts which come together under force and forms the blanks 8 into pads 10 which substantially conform to a portion of hip implant 17 as shown in FIG. 3. In the preferred embodiment, implant 17 includes a stem portion 16 which includes a reduced section forming shoulders 18 and 20. The reduced section is provided to accommodate the blanks. Shoulders 18 and 20 are provided to abut the distal and proximal ends of the blanks and assist in preventing the shaped pads 10 from shifting longitudinally relative to the implant 17. Once the blanks 8 are formed into shaped pads 10, the pads are placed onto the implant and temporarily held in place by a clamp device (not shown). Alternatively, a quantity of an adhesive polymer could be placed between the pads and stem to hold the pads in place during welding. The polymer would also assist in transferring the load to the stem in use. Once clamped to the implant, a laser is guided along the seams between the pads 10 forming a weld bead 22 to cause a portion of the pads to melt together thereby forming an integral pad about the body of the implant. As known in the welding industry, the intensity of the laser may be controlled to precisely control the depth of the weld bead. In the preferred embodiment, the intensity of the weld bead is set such that the bead is formed only between the porous pads and does not invade the outer surface of the implant. Once welded, the porous pads are securely held between the shoulders 18, 20 of the implant. To assist in the mechanical fixation of the stem the laser welder may be guided around the proximal and distal shoulder of the implant to weld the pad to the shoulder of the implant. Therefore, the interface between the pad and the implant is sealed by the laser weld. The sealing of the interface between the pad and the implant would prevent the ingress of the body fluids.

Figure 10:
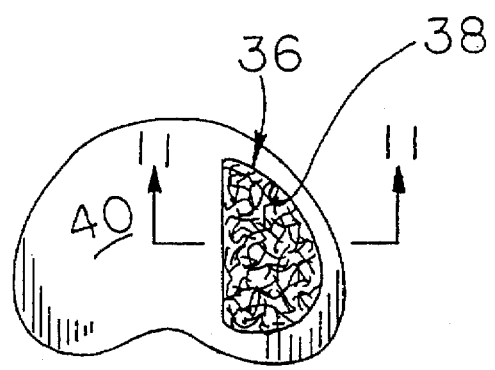
FIG. 10 is an elevational view illustrating the porous pad of FIGS. 6 through 10 positioned within a recess of a tibial plate.
Figure 11:
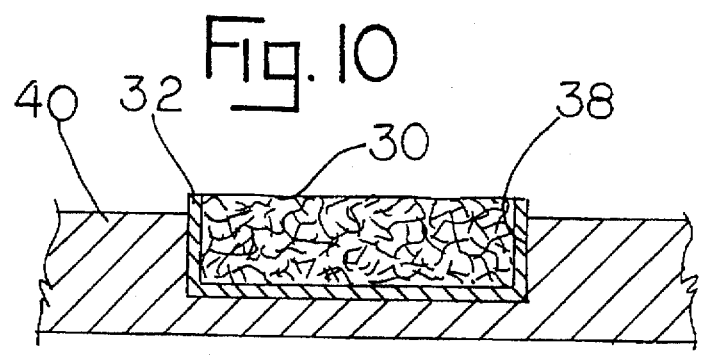
FIG. 11 is a cross sectional view taken along lines 11—11 of FIG. 10 and prior to welding.
Figure 12:
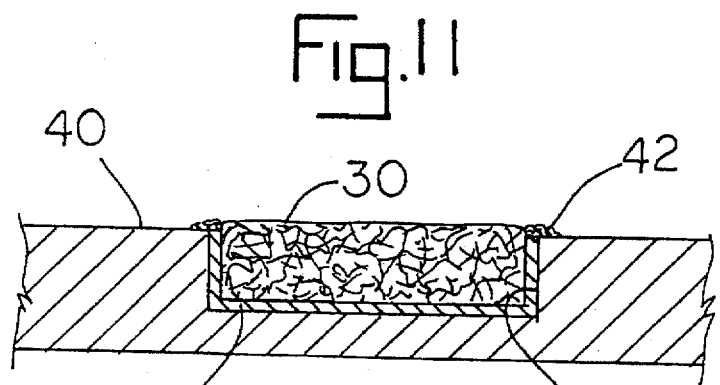
FIG. 12 illustrates the cross-sectional view of FIG. 11 after the porous pad has been laser welded to the implant.

An alternative method is illustrated in FIGS. 6 through 12. In the method of FIGS. 6–12, the porous material 30, preferably fiber metal, is cut to shape and then diffusion bonded to a thin metal foil 32 having a similar shape. The metal foil is slightly larger than the porous material and extends outwardly therefrom as illustrated. The fiber metal 30 and foil 32 are diffusion bonded in a known manner and are then placed into a stamping die 34 and stamped such that the portion of the foil extending outwardly from the fiber metal is bent around the side edges of the fiber metal as illustrated in FIGS. 8 and 9 to form a fiber metal pad 36 a foil bottom portion and side portions. The fiber metal pad 36 is placed within a matching recess 38 of an implant. In FIGS. 10 through 12, the fiber metal pad 30 is shown positioned within a matching recess 38 on the bone engaging surface of a tibial knee component 40 (partially illustrated). As illustrated, the fiber metal pad stands proud relative to the implant with the foil extending slightly above the implant surface. The small amount of foil extending above the implant provides the material which forms the weld bead 42 during the welding process. After positioning in the matching recess, the pad is laser welded to the implant at the junction between the implant and the foil along the edge of the pad. FIG. 12 illustrates the pad 36 after welding to the implant. The weld may be directed completely around the periphery of the fiber metal pad thereby sealing the area between the pad and the implant from the ingress of moisture. Further, the pad may be formed with openings to accommodate screw holes or fixation posts as are well known in the industry. Using the laser welding technique of the invention, the pad may be welded about such openings to enhance fixation of the pad to the implant.

Figure 12A:
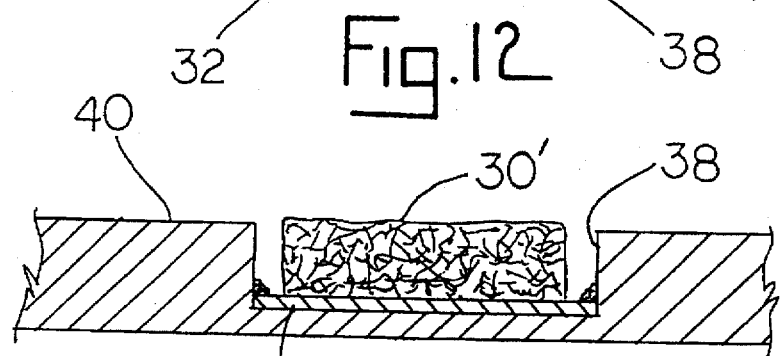
FIG. 12A illustrates an alternative method wherein the pad of FIG. 7 is placed into the recess and welded thereto without bending the extending edges upwardly.

In a preferred variation of the above method the stamping process is eliminated. Therefore, as illustrated in FIG. 12A, the foil 32' extends beyond the fiber metal layer 30' a predetermined amount but is shaped so as to closely approximate the cavity 38 formed in the implant 40. The laser beam is directed along the extending portion of the foil to secure the foil to the implant along the weld bead as illustrated in FIG. 12A.

FIG. 13 illustrates in diagram form the laser welding of the hip stem of FIGS. 1 through 5. The particular type of laser welder used is one of choice to the manufacturer and are commercially available. Given that laser welding in general is known, it will not be discussed here. What is important is that the power or intensity of the laser can be controlled such that the laser beam only affects the fiber metal pad locally and does not extend into implant substrate. Laser welding radiates less heat to the body of the implant than other welding techniques such as plasma or arc welding. Therefore the use of the laser is the preferred method to ensure that the metallurgy of the implant is not detrimentally changed by the welding process.

Figure 14B:
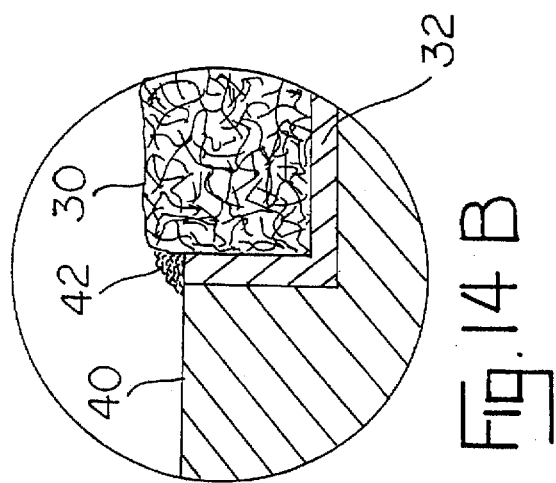
FIG. 14B is the enlarged cross sectional view of FIG. 14 after the porous pad has been welded to the implant.
Figure 14A:
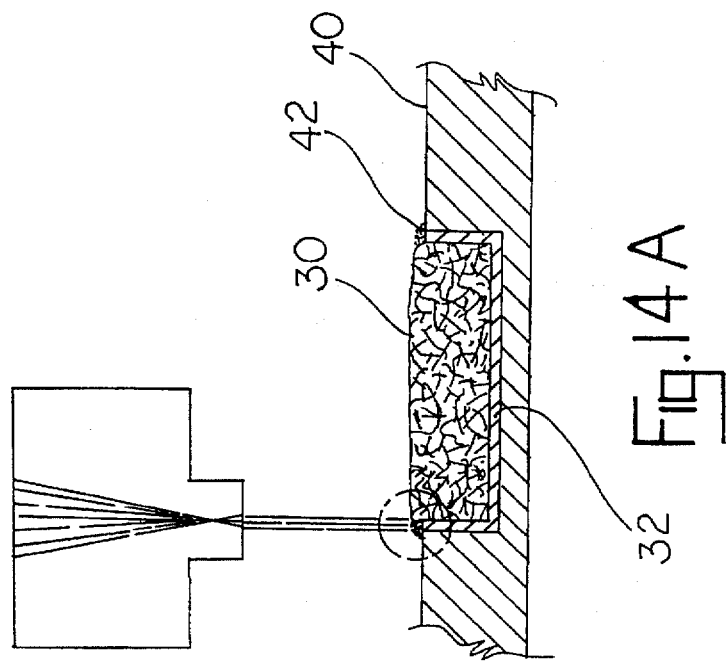
FIG. 14A is a diagram illustrating the method of laser welding the porous pads within the recess of an implant (only partially shown).

FIGS. 14 and 14A illustrate in diagram form the laser welding of the fiber metal pad of FIGS. 6 through 12. Here, since the welding process is joining the metal foil to the implant, some deformation of the implant is necessary to effect the weld. However, by use of the laser welder 50, the extent of the deformation will be localized along the weld bead, thereby preventing detrimental metallurgical changes in the implant body. As illustrated, a portion of the foil 32 extends above the implant surface and forms the material used in the welding process to form the weld bead 42. FIG. 14B illustrates the section of 14A after the welding process is completed.

Figure 15A:
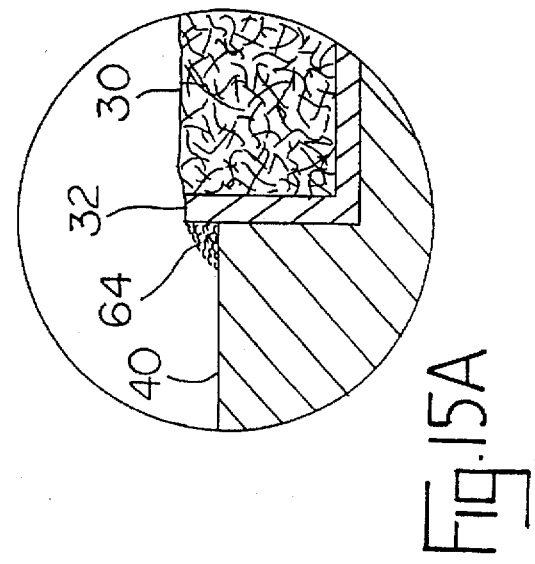
FIG. 15A is an enlarged cross sectional view illustrating the cladded junction between the porous pad and the implant.

FIG. 15 illustrates in diagram form laser cladding as an acceptable alternative to laser welding a fiber metal pad to an implant body. As is well known, laser cladding calls for the injection of metal powder 60 into the path of the laser beam 62. The laser beam 62 melts the powder and deposits the melted metal precisely on the implant. In the application of the current invention, the cladding process may be used in association with the embodiment of FIGS. 6 through 12 to fill in the space between the sides of the fiber metal pad and the implant. As the cladding process occurs, the molten metal deposited bonds the implant to the fiber metal pad at a point of contact and forms a fillet 64 of material as shown in FIG. 15A. Cladding could be a particular advantage in the process as the tolerances of the implant recess and the fiber metal pad could be reduced with any gap being filled in by the cladding process.

It should be understood that the cladding process utilized in keeping with the method of this invention could also be wire feed cladding or similar know processes for welding.

It should also be understood that the invention should not be limited to the precise details above but may be modified within the keeping of the appended claims.

We claim:

1. A method of forming an orthopaedic hip stem prosthesis having an annular porous surface, the method comprising the steps of;

a) providing an orthopaedic hip stem implant having a body including an elongated stem portion and a neck portion;

b) providing a first porous pad having a solid surface and a porous surface and including terminal edges;

c) forming the first porous pad to substantially conform to a portion of the implant body and stem;

d) providing a second porous pad having a solid surface and a porous surface and including terminal edges;

e) forming the second porous pad to substantially conform to a portion of the implant body and stem;

f) positioning the first porous pad and the second porous pad about the implant such that terminal edges of the first and second porous pads are adjacent; and g) forming a weld bead along the terminal edges to weld the first porous pad to the second porous pad such that the weld bead does not contact the body of the implant.

2. The method of claim 1, wherein the implant includes at least one annular shoulder, a refund edge of the first and second porous pad lying adjacent the shoulder.

3. The method of claim 2 including the step of welding the second mentioned edge of the first and second porous pad to the shoulder of the implant.

* * * * *